United States Patent [19]
Stouder, Jr.

[11] Patent Number: 5,746,720
[45] Date of Patent: May 5, 1998

[54] METHOD AND APPARATUS FOR INSERTION OF A CANNULA AND TROCAR

[76] Inventor: Albert E. Stouder, Jr., 318 N. West St., Tipton, Ind. 46072

[21] Appl. No.: 574,202

[22] Filed: Dec. 18, 1995

Related U.S. Application Data

[63] Continuation-in-part of Ser. No. 544,722, Oct. 18, 1995.

[51] Int. Cl.$^6$ .......................... A61M 5/00; A61M 5/178; A61M 5/32; A61M 29/00
[52] U.S. Cl. .................... 604/117; 604/158; 604/165; 604/175; 604/264; 606/191; 609/23
[58] Field of Search .......................... 604/117, 158, 604/164, 165, 179, 175, 198, 240, 241, 264, 283, 905

[56] References Cited

U.S. PATENT DOCUMENTS

| | | | |
|---|---|---|---|
| 3,817,251 | 6/1974 | Hasson | 128/348 |
| 4,636,199 | 1/1987 | Victor | 604/164 |
| 4,869,717 | 9/1989 | Adair | 604/51 |
| 4,895,564 | 1/1990 | Farrell | 604/164 |
| 4,994,036 | 2/1991 | Biscoping et al. | 604/158 |
| 5,120,318 | 6/1992 | Nallaparedy | 604/164 |
| 5,137,509 | 8/1992 | Freitas | 604/26 |
| 5,139,485 | 8/1992 | Smith et al. | 604/158 |
| 5,158,543 | 10/1992 | Lazarus | 604/164 |
| 5,169,387 | 12/1992 | Kronner | 604/51 |
| 5,176,697 | 1/1993 | Hasson et al. | 606/191 |
| 5,261,891 | 11/1993 | Brinkerhoff et al. | 604/165 |
| 5,273,545 | 12/1993 | Hunt et al. | 604/167 |
| 5,290,247 | 3/1994 | Crittenden | 604/171 |
| 5,304,141 | 4/1994 | Johnson et al. | 604/158 |
| 5,399,167 | 3/1995 | Deniega | 604/164 |
| 5,423,760 | 6/1995 | Yoon | 604/165 |
| 5,569,204 | 10/1996 | Cramer | 604/164 |
| 5,609,562 | 3/1997 | Kaali | 604/114 |

OTHER PUBLICATIONS

"IOTEC Trocars; Line up for Sharp Savings"; Iotec Industries brochure, 1995.

*Primary Examiner*—Michael Powell Buiz
*Assistant Examiner*—Chalin Smith
*Attorney, Agent, or Firm*—Woodard, Emhardt, Naughton Moriarty & McNett

[57] ABSTRACT

An adjustable length cannula which may be longitudinally extended or retracted in order to accommodate a range of body cavity wall thicknesses. A method for inserting the cannula is disclosed, in which a guiding cannula is placed into the peritoneal cavity using the insufflation needle as a guidewire, and a screw dilator and cannula are then placed into the peritoneal cavity using the guiding cannula as a guidewire. The guiding cannula also allows visual inspection of the peritoneal cavity with an endoscope prior to insertion of the dilator/cannula in order to verify proper clearance.

23 Claims, 8 Drawing Sheets

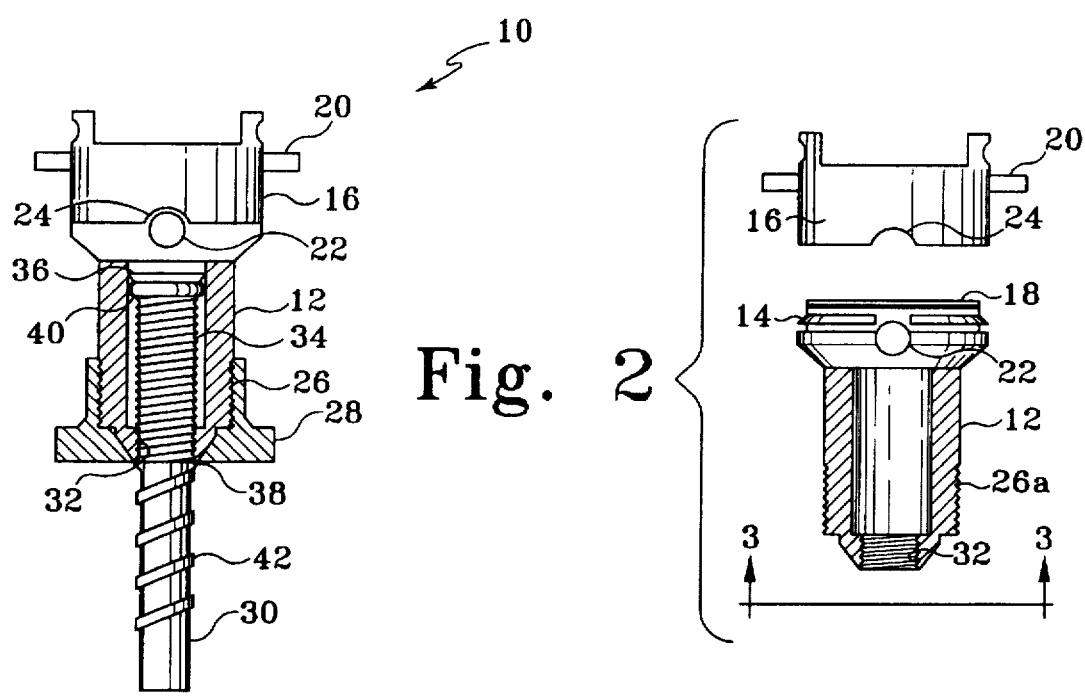
Fig. 1
Fig. 2
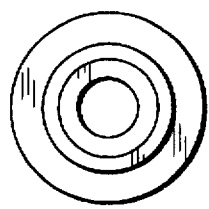
Fig. 3
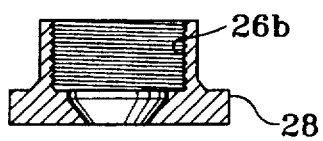
Fig. 4
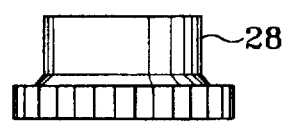
Fig. 5
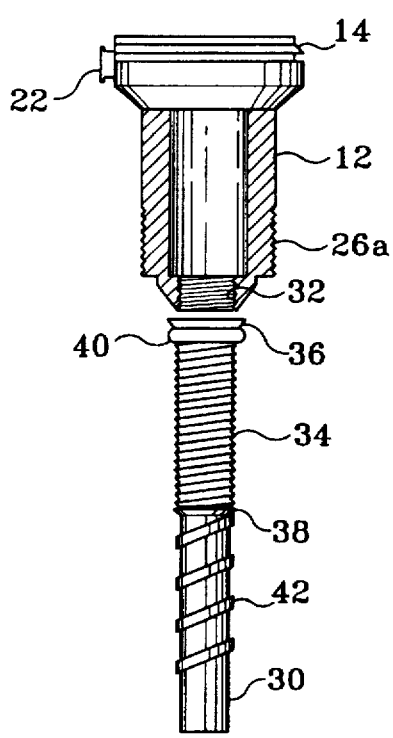
Fig. 6

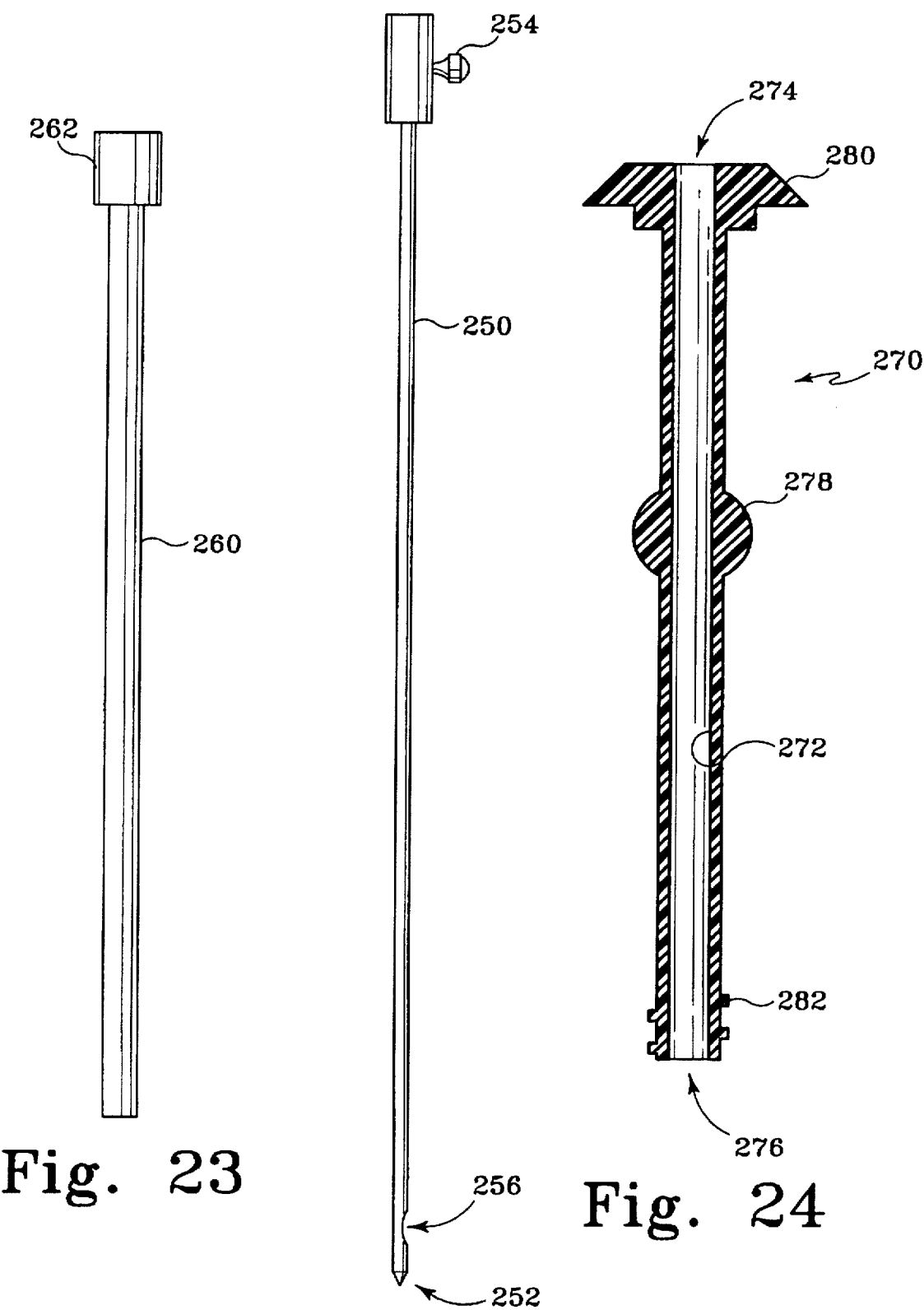

METHOD AND APPARATUS FOR INSERTION OF A CANNULA AND TROCAR

CROSS-REFERENCE TO RELATED APPLICATIONS

The present application is a continuation-in-part of application Ser. No. 08/544,722, entitled ADJUSTABLE LENGTH CANNULA AND TROCAR, filed by the same inventor on Oct. 18, 1995.

TECHNICAL FIELD OF THE INVENTION

The present invention generally relates to cannulas and trocars used to puncture tissue for the performance of laparoscopic or arthroscopic surgery and, more particularly, to a method and apparatus for insertion of a cannula and trocar.

BACKGROUND OF THE INVENTION

Prior to laparoscopic or arthroscopic surgery, a cannula is inserted through the skin to access a body cavity through the cannula tube. In order to penetrate the skin, the distal end of the cannula tube is placed against the skin and a trocar is inserted through the tube. By pressing against the proximal end of the trocar, the point of the trocar is forced through the skin until it enters the body cavity. At this time, the cannula tube in inserted through the perforation made by the trocar and the trocar is withdrawn, leaving the cannula tube as an access way into the body cavity.

It has been found that often a great deal of force is required to cause the trocar point to penetrate the skin and underlying tissue. When the point finally breaks through this tissue, resistance to penetration is suddenly removed, and the trocar point can suddenly penetrate to reach internal organs of the body, which may cause lacerations and other injury to the internal organs.

For this reason, when a laparoscopy is performed, a pneumoperitoneum is first performed by introducing into the peritoneal cavity 3–4 liters of $CO_2$. The pneumoperitoneum causes rising of the front abdominal wall and separation of the internal organs thereof and in particular, if the patient is placed into a slight Trendelemburg's position, the internal organs tend to move to the upper abdominal region. The trocar needle must then be introduced at an angle of 45° in the lower periumbilical seat after sectioning of the skin (in a semi-circle around the lower edge of the navel) and the subcutis until reaching the aponeurosis. In addition, the trocar must be pushed carefully to avoid sudden deep penetration which could injure the internal organs or large vessels. However, despite all of these precautions, it is not always possible to avoid traumatic complications of the anatomic structures mentioned above and the complications connected with the pneumoperitoneum.

An additional problem in current laparoscopic procedures is that the thickness of abdominal tissue which must be traversed by the cannula tube varies from patient to patient. Because of this, a variety of different length cannulas are available for use in laparoscopic procedures, requiring the doctor to estimate the thickness of the abdominal tissue for the particular patient and then select a cannula having the proper length. Additionally, the present fixed length cannulas also contain no means for stabilizing the cannula against the surface of the patient's body. The result is that movement of the cannula during the laparoscopic procedure can cause tissue trauma in the area of skin surrounding the cannula. The surgeon performing the laparoscopic procedure must therefore stabilize the top of the cannula tube with one hand while using the other hand to insert the laparoscopic instrument into the cannula tube. Finally, present cannula tubes protrude from the skin's surface a substantial distance, which contributes to their general instability, easily becoming entangled in tubes and other devices used in the surgical procedure.

There is therefore a need in the prior art for a cannula tube which may be used to penetrate varying thicknesses of abdominal tissue, which provides a stable interface between the cannula and the patient and which exhibits a low profile above the surface of the patient's skin. Additionally, there is a need in the prior art for a trocar which will minimize the chance of accidental trauma to the abdominal organs due to penetration of the trocar to too great a depth within the abdominal cavity. The present invention is directed toward meeting these needs.

SUMMARY OF THE INVENTION

The present invention relates to an adjustable length cannula which may be longitudinally extended or retracted in order to accommodate a range of body cavity wall thicknesses. A method for inserting the cannula is disclosed, in which a guiding cannula is placed into the peritoneal cavity using the insufflation needle as a guidewire, and a screw dilator and cannula are then placed into the peritoneal cavity using the guiding cannula as a guidewire. The guiding cannula also allows visual inspection of the peritoneal cavity with an endoscope prior to insertion of the dilator/cannula in order to verify proper clearance.

In one form of the invention, a method for inserting a cannula through a body cavity wall and into a body cavity is disclosed, comprising the steps of: (a) inserting a guide cannula through the body cavity wall such that a distal end of the guide cannula extends into the body cavity; and (b) inserting a hollow dilator sleeved within a cannula through the body cavity wall over the guide cannula, such that a distal end of the dilator and a distal end of the cannula extend into the body cavity.

In another form of the invention, a method for inserting a cannula through a body cavity wall and into a body cavity is disclosed, comprising the steps of: (a) inserting an insufflation needle through the body cavity wall such that an opening near a distal end of the insufflation needle is within the body cavity; (b) flowing gas through the opening and into the body cavity in order to insufflate the body cavity; (c) inserting a guide cannula over the insufflation needle and through the body cavity wall such that a distal end of the guide cannula is within the body cavity; (d) withdrawing the insufflation needle from the body cavity; (e) inserting a dilator sleeved within a cannula through the body cavity wall over the guide cannula, such that a distal end of the dilator and a distal end of the cannula extend into the body cavity; (f) withdrawing the guide cannula from the body cavity; and (g) withdrawing the dilator from the body cavity.

In another form of the invention, a method for inserting a cannula through a body cavity wall and into a body cavity is disclosed, comprising the step of: (a) sleeving a guide cannula over an insufflation needle; (b) sleeving a dilator over the guide cannula; (c) sleeving a cannula over the dilator; (d) inserting the insufflation needle through the body cavity wall such that an opening near a distal end of the insufflation needle is within the body cavity; (e) flowing gas through the opening and into the body cavity in order to insufflate the body cavity; (f) advancing the guide cannula over the insufflation needle and through the body cavity wall; (g) withdrawing the insufflation needle from the body cavity; and (h) advancing the dilator and the cannula over the guide cannula and through the body cavity wall.

BRIEF DESCRIPTION OF THE DRAWINGS

FIG. 1 is a partial cross-sectional side view of a first embodiment adjustable length cannula of the present invention.

FIG. 2 is a partial cross-sectional side view of a cap and body member of the first embodiment adjustable length cannula of the present invention.

FIG. 3 is a bottom plan view of the body member of the first embodiment adjustable length cannula of the present invention.

FIG. 4 is a cross-sectional view of a collet clamp of the first embodiment adjustable length cannula of the present invention.

FIG. 5 is a side elevational view of the collet clamp of the first embodiment adjustable length cannula of the present invention.

FIG. 6 is a partial cross-sectional side view of the body member and cannula member of the first embodiment adjustable length cannula of the present invention.

FIG. 22 is a side elevational view of an insufflation needle.

FIG. 23 is a side elevational view of a guide cannula of the present invention.

FIG. 24 is a side cross-sectional view of a third embodiment trocar of the present invention.

DETAILED DESCRIPTION OF THE PREFERRED EMBODIMENTS

Figure 7:
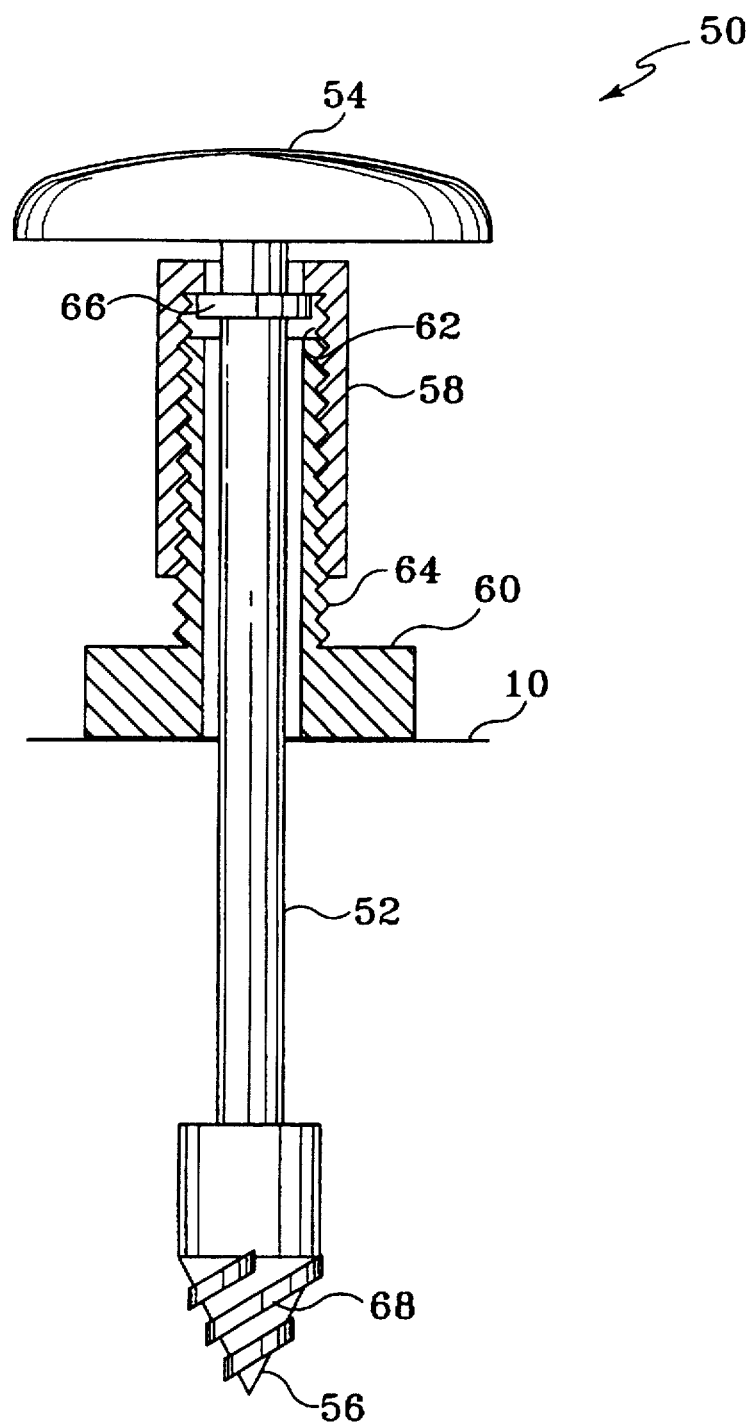
FIG. 7 is a partial cross-sectional side view of a first embodiment adjustable length trocar of the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

The present invention involves the use of a single cannula which may be adjusted to any desired length within a fixed range. Such adjustability allows the cannula to be used with a variety of body cavity wall thicknesses. A first embodiment of such an adjustable length cannula is illustrated in partial cross-sectional side view in FIG. 1 and is indicated generally at 10. Adjustable length cannula 10 comprises a body member 12 which is generally cylindrical in shape and illustrated in a partial cross-sectional view in FIGS. 1, 2 and 6. The body member 12 preferably includes either ridges or threads 14 near a top surface thereof in order to facilitate connection of a cap 16. Lying between the body member 12 and the cap 16 is a suitable main seal 18, such as a silicone slit seal, which helps to provide an airtight seal around instruments which are passed through the central channel of the adjustable length cannula 10. Furthermore, the cap 16 includes a slide 20 disposed therethrough, the slide 20 containing a plurality of secondary seals of various sizes in order to accommodate instruments of varying diameter which may be passed through the adjustable length cannula 10. The slide 20 is preferably constructed in accordance with the teachings of U.S. Pat. No. 5,350,362, issued to the same inventor as the present application. The body member 12 optionally includes a side port 22 which communicates between the exterior and interior of the body member 12, as is known in the art. If the optional side port 22 is present, then the cap 16 preferably includes a notch 24 in order to provide clearance for the side port 22.

Attached to the exterior of the body member 12 by means of threads 26 is a collet clamp 28. As will be explained in greater detail hereinbelow, the collet clamp 28 provides a stable platform for the adjustable length cannula in order to minimize trauma to the surrounding tissue.

The adjustable length cannula 10 further includes a sliding cannula member 30 which is adjustably engaged with the body member 12 by means of interaction between incremental spacing members 32 on the body member 12 and incremental spacing members 34 on the cannula member 30. In order to provide adjustability of the longitudinal position of the cannula member 30 within the body member 12, the incremental spacing members 32 and 34 may comprise complementary threaded surfaces. Alternatively, the incremental spacing members 32 may comprise one or more raised ribs while the incremental spacing members 34 may comprise a plurality of indentations, or vise versa. It will therefore be appreciated by those skilled in the art that interaction between the incremental spacing members 32 and 34 allow the cannula member 30 to be extracted from or inserted into the body member 12 over a limited range in order to adjust the longitudinal length of the adjustable length cannula 10. The raised lips 36 and 38 on the cannula member 30 limit the longitudinal travel of the cannula member 30 into and out of the body 12. The cannula member 30 carries an O-ring seal 40 in order to prevent passage of gases or liquids around the exterior of the cannula member 30.

The cannula member 30 further includes an external thread 42 around the distal section thereof, in order to facilitate insertion of the adjustable length cannula 10 and retention thereof within the body cavity during the laparoscopic procedure. In operation, the relative positioning of incremental spacing members 32 and 34 is adjusted in order to lengthen or shorten the adjustable length cannula 10 to a longitudinal dimension appropriate for the patient. A trocar (not shown) is then inserted through the slide seal 20, the main seal 18 and through the central channel of the cannula member 30 until the pointed distal tip of the trocar protrudes from the distal end of the cannula member 30. The adjustable length cannula 10 is then inserted through the patient's abdominal tissue (for example) with a pushing and twisting motion until the annular flange at the bottom of the collet clamp 28 reaches the surface of the patient's skin. Because the contact of the collet clamp 28 with the patient's skin prevents further insertion of the adjustable length cannula 10, the danger of inserting the trocar/adjustable length cannula 10 too far into the abdominal cavity, thereby potentially injuring intra-abdominal organs, is eliminated.

Furthermore, the action of the screw thread 42 as the adjustable length cannula 10 is inserted through the abdominal tissue tends to compress the abdominal wall in the area of insertion between the thread 42 and the collet clamp 28. The result is that the abdominal tissue is compressed between the outer skin and the fascia in the area of the adjustable length cannula 10, thereby providing greater stability to the adjustable length cannula 10. Furthermore, the broad surface area of the collet clamp 28 provides a stable platform to prevent excessive motion of the adjustable length cannula 10 after insertion. Not only do these features reduce tissue trauma of the abdominal wall due to decreased movement of the adjustable length cannula 10, but they also obviate the need for the surgeon to steady the cannula with one hand while inserting, operating and extracting instruments through its central channel. A further advantage of the adjustable length cannula 10 is that a single cannula may be used for a wide range of abdominal wall thicknesses.

Referring now to FIG. 7, there is shown a first embodiment adjustable length trocar of the present invention indicated generally at 50. Because the adjustable length cannula 10 of FIG. 1 may be adjusted to a wide range of longitudinal lengths, it is necessary to provide a trocar for use with the adjustable length cannula which may also be adjusted in longitudinal length. The trocar 50 of FIG. 7 incorporates this feature. The trocar 50 consists of a longitudinal shaft 52 terminated by a disc-shaped handle 54 at its proximal end and a pointed tip 56 at its distal end. The trocar shaft 52 is partially contained within an upper trocar housing 58 and a lower trocar housing 60. The relative longitudinal positions of upper trocar housing 58 and lower trocar housing 60 are adjustable within a limited range by interaction of the threads 62 and 64.

The trocar shaft 52 includes an annular flange 66 fixedly attached thereto. Because the upper surface of the upper trocar housing 58 is held between the annular flange 66 and the trocar handle 54, the longitudinal length of the adjustable length trocar 50 (between the bottom surface of the trocar housing 50 and the distal tip 56) may be adjusted by varying the position of the upper trocar housing 58 with respect to the lower trocar housing 60. The bottom surface of the bottom trocar housing 60 rests on the upper surface of the adjustable length cannula 10, and the threads 62 and 64 are adjusted until the tip 56 of the adjustable length trocar 50 extends through the distal portion of cannula member 30. Once such positioning has been achieved, then the combination adjustable length cannula 10 and adjustable length trocar 50 may be inserted into the patient as described above. The adjustable length trocar 50 may optionally be provided with an auger screw thread 68 on the pointed distal tip 56 in order to facilitate insertion of the adjustable length trocar 50 through the abdominal wall. A very controlled insertion may be achieved by twisting the adjustable length trocar 50 and the adjustable length cannula 10, thereby allowing the screw threads 68 and 42 to draw the device into the abdominal wall. This provides a much more precise insertion than the prior art devices in which the pointed trocar is simply pushed through the abdominal wall.

Figure 8:
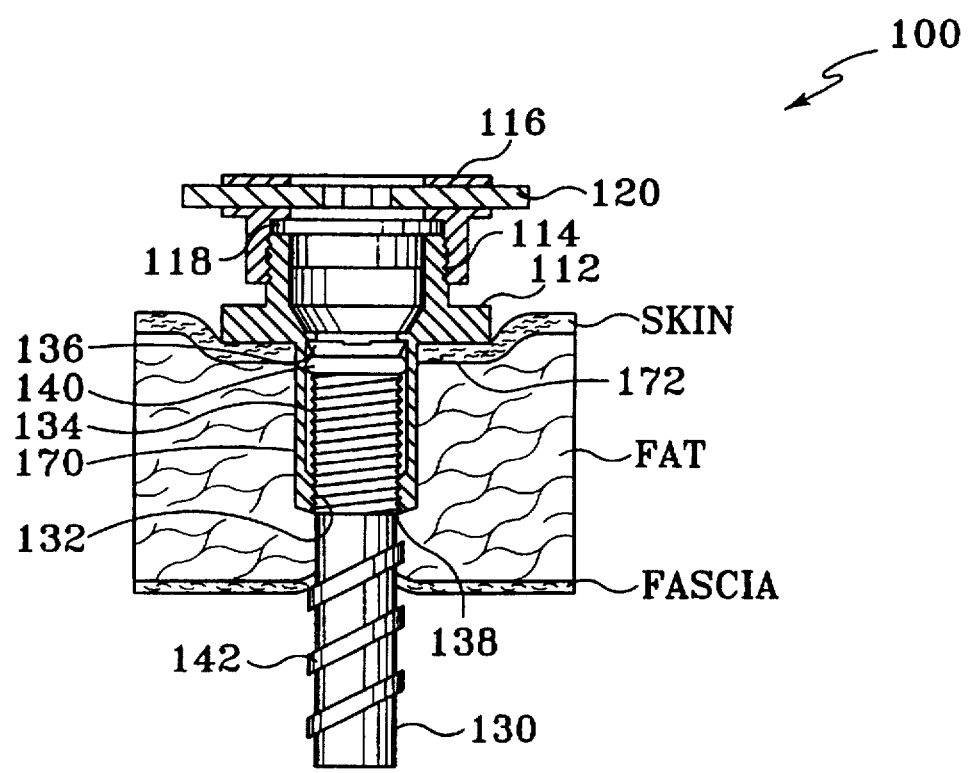
FIG. 8 is a partial cross-sectional side view of a second embodiment adjustable length cannula of the present invention inserted through a wall of a body cavity.
Figure 13:
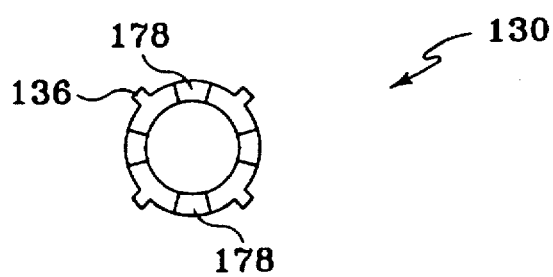
FIG. 13 is a top plan view of the cannula member of FIG. 12.

Referring now to FIG. 8, a second embodiment variable length cannula is illustrated in partial cross-sectional side view, and indicated generally at 100. The adjustable length cannula 100 is shown inserted through a patient's abdominal wall, comprising a skin layer, a fat layer and a fascia layer. The adjustable length cannula 100 includes a body member 112 to which is mounted a cap 116 by means of the engaged threads 114. As with the first embodiment adjustable length cannula 10, the adjustable length cannula 100 includes a slide seal 120 which allows the adjustable length cannula 100 to be sealed against laparoscopic instruments having varying diameters. Further sealing is provided by a main seal 118 which is positioned between the body member 112 and the cap 116. Situated partially within the body member 112 is a cannula member 130, incremental spacing members 132 on the body member 112 and 134 on the cannula member 130, such as complementary raised ribs and indentations or complementary screw threads, allow the longitudinal position of the cannula member 130 with respect to the body member 112 to be adjusted, thereby providing a variable length to the cannula 100. The range of motion of the cannula member 130 is limited by at least one stopper member 136 (see FIG. 13) and a lower raised lip 138. A rubber O-ring seal 140 provides sealing between the cannula member 130 and the body member 112. Cannula member 130 is also provided with a screw thread 142 in order to aid in insertion of the adjustable length cannula 100.

The adjustable length cannula 100 is illustrated in FIG. 8 adjusted to its shortest longitudinal length and inserted through a relatively thin abdominal wall section. It will be appreciated by those skilled in the art that the adjustable length cannula 100 presents a very low profile above the surface of the patient's skin owing to the fact that the body member includes a subcutaneous portion 170, which provides for the adjustability in the length of the cannula 100, lies completely below the surface of the patient's skin. The body member 112 further includes an annular flange portion 172 above the subcutaneous portion 170 which performs the same function as the collet clamp 28 of the first embodiment adjustable length cannula 10 of FIG. 1. As illustrated in FIG. 8, the skin, fat and fascia of the abdominal wall tissue are compressed between the screw threads 142 and the annular flange 172 of the body member 112, thereby providing stability to the adjustable length cannula 100 as well as minimizing tissue trauma in the area of the cannula placement. The low external profile of the adjustable length cannula 100 further reduces accidental movement of the cannula 100, thereby further reducing tissue trauma in the area surrounding the cannula.

Figure 9:
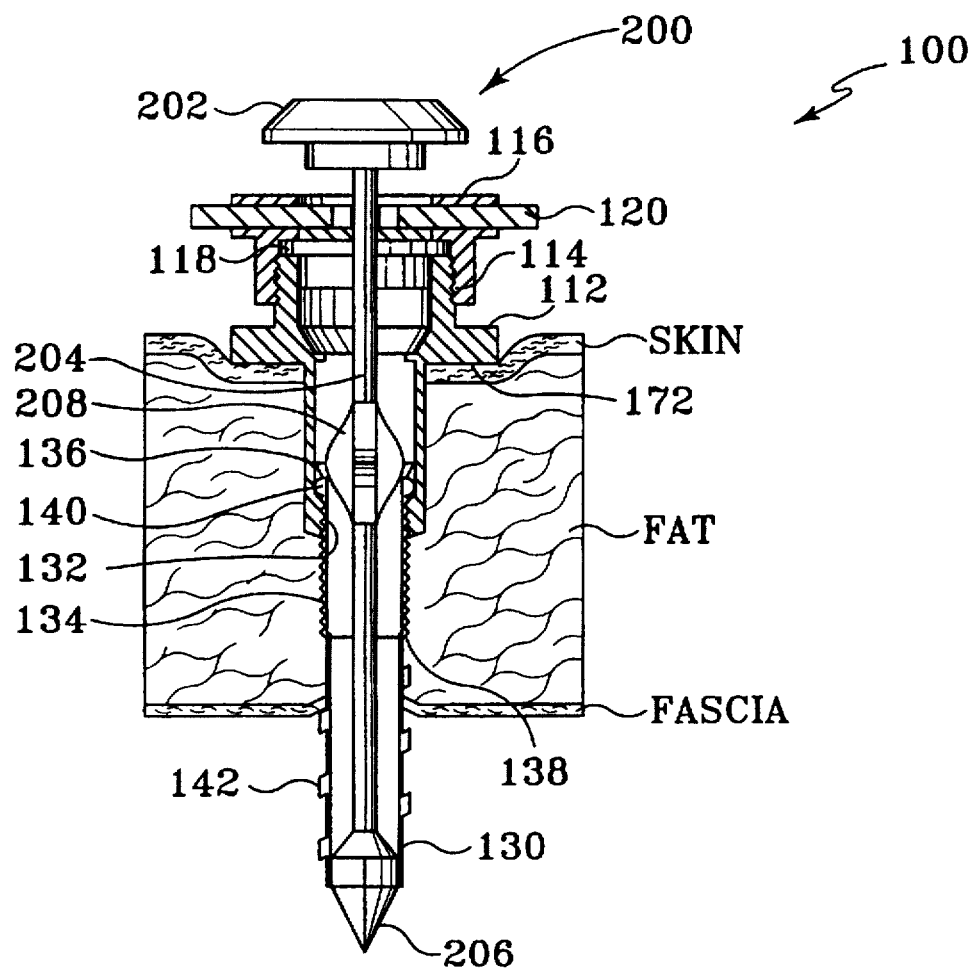
FIG. 9 is a partial cross-sectional side view of the second embodiment adjustable length cannula of the present invention assembled with a second embodiment trocar of the present invention.

Referring now to FIG. 9, the adjustable length cannula 100 is shown in combination with a trocar 200. The trocar 200 includes a disc-shaped handle 202, a longitudinal shaft 204, and a pointed distal end 206. The trocar 200 includes four extensions (or fins) 208 which engage complementary notches 178 in the top of cannula member 130 (see FIG. 13) in order to allow a twisting force to be applied to the cannula member 130. The fins 208 are positioned on the trocar shaft 204 at a position where the pointed distal tip 206 will protrude from the distal end of the cannula member 130 when the fins 208 are engaged with the notches 178 on the top of the cannula member. Engagement of the fins 208 with the cannula member 130 also prevents the trocar 200 from being pushed any further from the distal end of the adjustable length cannula 100.

The adjustable length cannula 100 may be inserted into the patient's body by two different methods. One method of insertion is to insert short. In this method, the cannula member 130 is retracted completely within the body member 112 and the trocar 200 is placed within the adjustable length cannula 100. The trocar 200/cannula 100 is then inserted in the normal fashion until the annular flange 172 of the body member 112 abuts the patient's skin. At this point, the motion is changed to a clockwise rotation of the trocar 200, which in turn creates a clockwise rotation of the cannula member 130. Such rotation causes the cannula member 130 to be extracted from the body member 112 by action of the complementary screw threads 132 and 134. Additionally, as the cannula member 130 is extracted from the body member 112, the screw thread 142 on the cannula member 130 works its way through the abdominal tissue. Such rotation is continued until the tip of the cannula member 130 enters the abdominal cavity. At this point, the adjustable length cannula 100 has been inserted as far as desired by rotation of the trocar 200. By having the wide annular flange 172 of the body member 112 resting on the surface of the skin, there will be no sudden, uncontrolled penetration of the abdominal cavity as with the prior art instruments.

The second method of insertion of the adjustable length cannula 100 is to insert long. In this method, the adjustable length cannula 100 is extended to the desired length and the prior art cannula insertion method is followed until the desired penetration of the abdominal cavity has been achieved. At this point, the body member 112 is rotated while holding the trocar 200 (and consequently the cannula member 130) stationary. Such rotation causes the body member 112 to be screwed down into the patient until the annular flange 172 rests upon the skin, thereby providing a snug fit.

Whether the adjustable length cannula 100 is inserted short or long, when the cannula is in the desired position the trocar is removed. Compression of the patient's skin and fat between the thread 142 and the annular flange surface 172 of the body member 112 establishes a relatively fixed instrument so that there is little lateral instability. This will minimize tissue trauma in the area surrounding insertion and will allow insertion of a surgical instrument through the cannula without the need to steady the cannula with a second hand.

Figure 10:
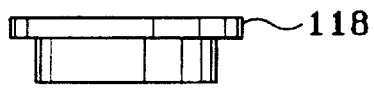
FIG. 10 is a side elevational view of a main valve of the second embodiment adjustable length cannula of the present invention.
Figure 11:
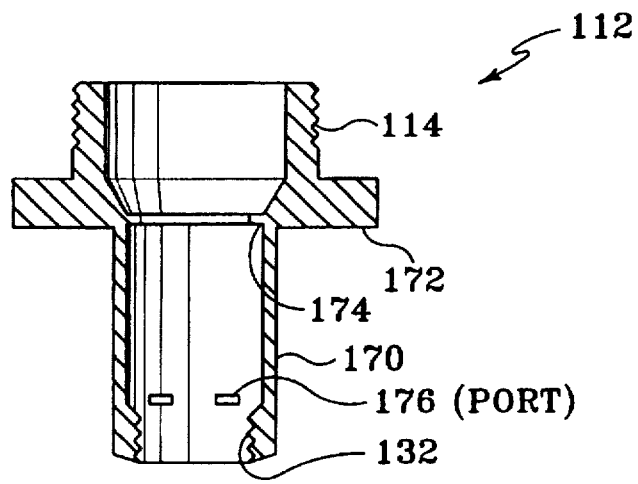
FIG. 11 is a cross-sectional side view of a body member of the second embodiment adjustable length cannula of the present invention.

Referring now to FIG. 10, the main seal 118 is shown in a side elevational view. The main seal 118 is preferably formed from silicone or similar materials and includes a slit therethrough in order to allow passage of the trocar 200 and surgical instruments. Referring to FIG. 11, the body member 112 is illustrated in cross-section. A protruding annular ledge 174 is clearly visible in the view of FIG. 11. The ledge 174 interacts with the stopper members 136 of the cannula member 130 in order to prevent the cannula member 130 from moving in the proximal direction beyond the ledge 174 and hitting the main seal 118. The body member 112 optionally includes a plurality of air ports 176 in order to aid in sterilization of the body member 112.

Figure 12:
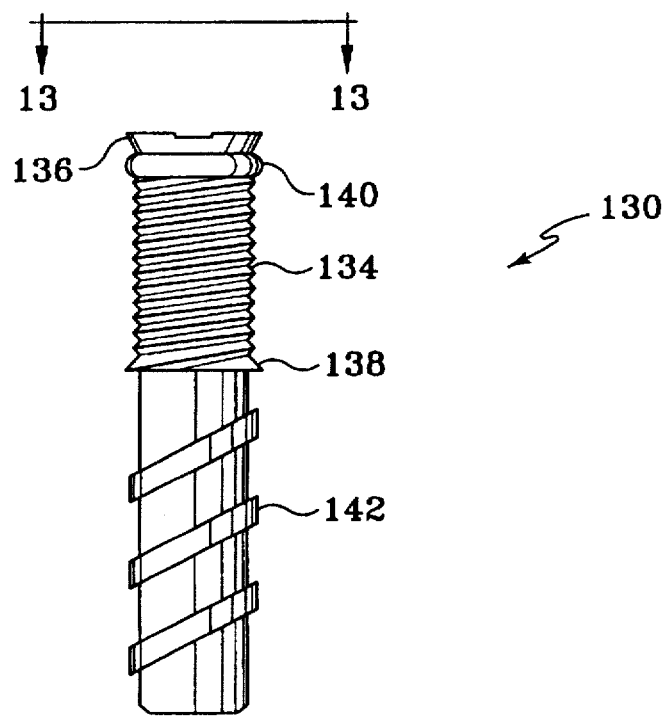
FIG. 12 is a side elevational view of a cannula member of the second embodiment adjustable length cannula of the present invention.

Referring to FIG. 12, the cannula member 130 is illustrated in a side elevational view. The cannula member 130 is inserted into the proximal end of the body member 112. The top stoppers 136 of the cannula member 130 will bend during insertion into the body member 112 and then snap back into position once the cannula member 130 has been inserted into the body member 112. Thereafter, interaction between the top stoppers 136 and the ledge 174 prevent the cannula member 130 from backing out of the top of the body member 112. The cannula member 130 is illustrated in a top plan view in FIG. 13. Notches 178 formed into the top surface of the cannula 130 are clearly visible in this view. The notches 178 engage the fins 208 of the trocar 200 in order to lock the trocar 200 to the cannula 130 for rotation therewith.

Figure 14:
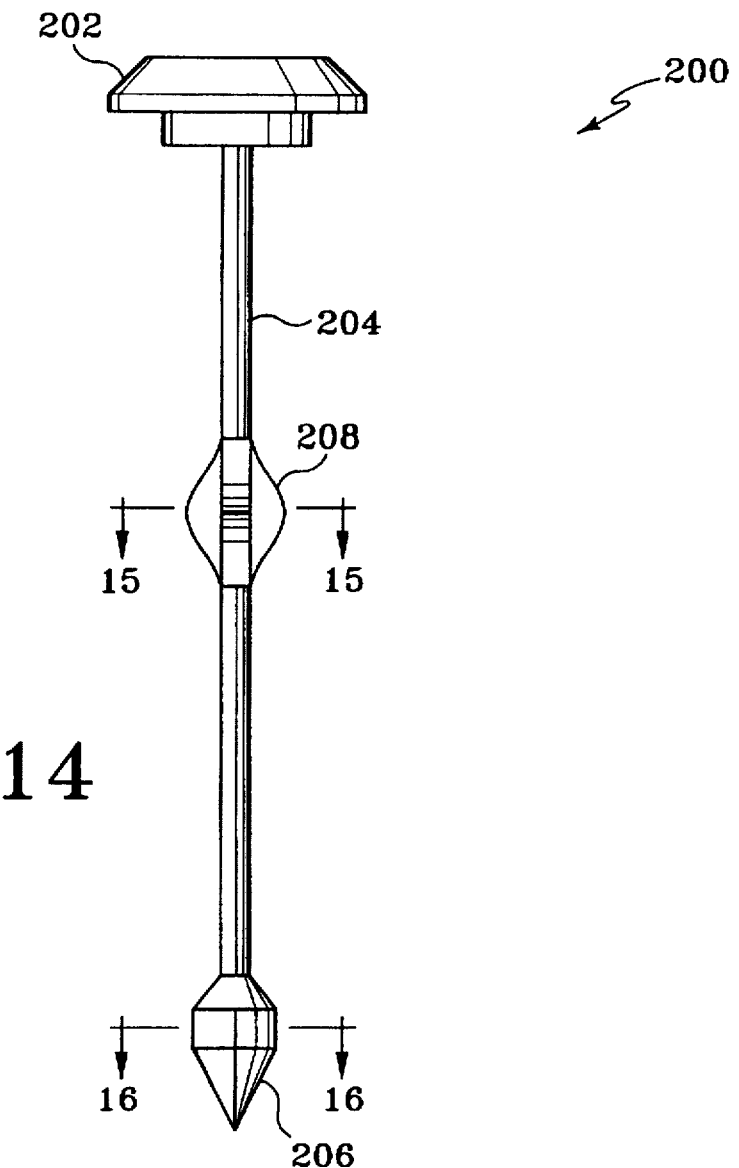
FIG. 14 is a side elevational view of the second embodiment trocar of the present invention.
Figure 15:
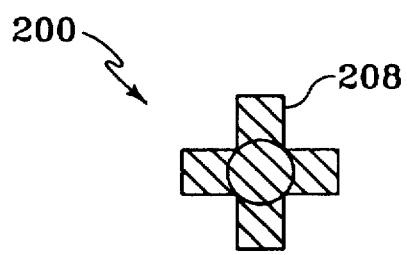
FIG. 15 is a first cross-sectional view of the trocar of FIG. 14.
Figure 16:
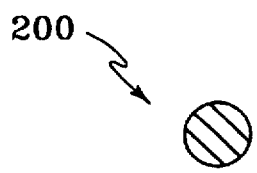
FIG. 16 is a second cross-sectional view of the trocar of FIG. 14.
Figure 17:
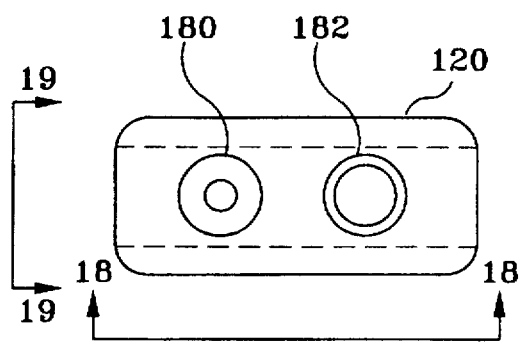
FIG. 17 is a top plan view of a slide seal of the second embodiment adjustable length cannula of the present invention.
Figure 18:
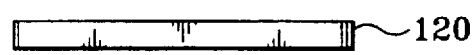
FIG. 18 is a first side elevational view of the slide seal of FIG. 17.
Figure 19:
FIG. 19 is a second side elevational view of the slide seal of FIG. 17.
Figure 20:
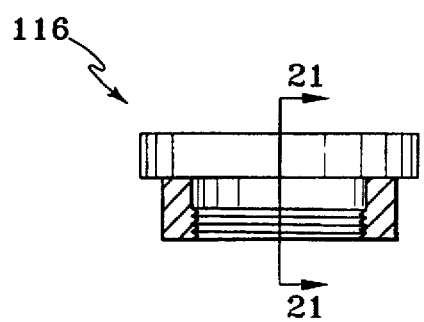
FIG. 20 is a partial cross-sectional side view of a cap of the second embodiment adjustable length cannula of the present invention.
Figure 21:
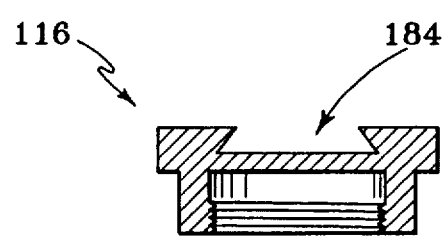
FIG. 21 is a cross-sectional view of the cap of the second embodiment adjustable length cannula of the present invention.

Referring now to FIGS. 14-16, the trocar 200 is illustrated separated from the adjustable length cannula 100. Referring now to FIG. 17, a first embodiment of the slide seal 120 is illustrated in a top plan view. The first embodiment of the slide seal 120 includes a first seal 180 to accommodate relatively narrow instruments and a second seal 182 to accommodate relatively wide instruments. A first side elevational view of the slide seal 120 is illustrated in FIG. 18, while a second side view of the slide seal 120 is illustrated in FIG. 19. The cap 116 is illustrated in a partial cross-sectional side view in FIG. 20, and in a full cross-sectional second side view in FIG. 21. A slot 184 is formed in the cap 116 in order to accommodate the slide seal 120.

The adjustable length cannula 100 preferably measures 0.68 inches from the skin surface to the top of the cannula 100, 2.6 inches from the skin surface to a distal end of the cannula member 130 in a fully extended position, and 2.1 inches from the skin surface to the distal end of the cannula member 130 in a fully retracted position. Unless otherwise indicated, all of the items disclosed in the present application (except for the seals) may be constructed from plastic, stainless steel, or any other biocompatible material. Additionally, the devices may be disposable or reuseable after sterilization.

A third method for insertion of the adjustable length cannula 100 utilizes the additional apparatus illustrated in FIGS. 22-24. In FIG. 22, a commonly available Verres insufflation needle 250 is illustrated. The insufflation needle 250 includes a sharp tip 252 and a longitudinal lumen (not shown) which couples the insufflation gas port 254, which may be connected to a source of insufflation gas, and the gas delivery hole 256 near the distal end of the needle 250. Referring now to FIG. 23, there is illustrated a guide cannula 260 which includes a central longitudinal lumen (not shown) adapted to receive the insufflation needle 250 in a sliding fit. The guide cannula 260 may be made from any pliable material, such as a pliable plastic. A valve 262 is coupled to the proximal end of the guide cannula 260 in order to provide an airtight seal around any instrument which is inserted into the guide cannula 260. Valve 262 is preferably a silicone slit valve. Finally, a screw dilator 270 is illustrated in FIG. 24 in cross-section. The screw dilator 270 is similar to the trocar 200 of FIG. 14 with the exception that the screw dilator 270 includes a central lumen 272 therein extending from the open proximal end 274 to the open distal end 276. The screw dilator 270 includes fins 278 similar to the fins 208 of the trocar 200. The fins 278 are designed to engage the notches 178 of the cannula member 130 (see FIG. 13). The screw dilator 270 further includes a handle 280 at a proximal end thereof and an external thread 282 at a distal end thereof.

In the third embodiment insertion method, the insufflation needle 250 is longitudinally disposed within the central lumen of the guiding catheter 260, such that the valve 262 is sealed around the needle 250. In a preferred embodiment, the insufflation needle 250 extends from the distal end of the guiding cannula 260 by approximately 1.5 inches. The combined insufflation needle 250 and guiding cannula 260 are then longitudinally disposed within the lumen 272 of the screw dilator 270. Finally, the combined screw dilator 270, guide cannula 260 and insufflation needle 250 are longitudinally disposed within the central lumen of the adjustable length cannula 100. Once assembled, the threads 282 of the screw dilator 270 extend from the distal end of the cannula 100, the guide cannula 260 extends from the distal end of the screw dilator 270, and the insufflation needle 250 extends from the distal end of the guide cannula 260.

Once the device has been assembled as detailed above, a supply of $CO_2$ gas is coupled to the coupling 254 and a pneumoperitoneum is performed by inserting the insufflation needle 250 into the peritoneal cavity. Once the insufflation needle 250 has penetrated the peritoneal cavity, 3–4 liters of $CO_2$ may be introduced into the cavity through the distal hole 256 of the insufflation needle 250. The pneumoperitoneum causes rising of the front abdominal wall and separation of the internal organs thereof. Once the peritoneal cavity has been properly insufflated, the guiding cannula 260 is moved in a distal direction until a sharp increase in the $CO_2$ gas pressure is indicated. Such a pressure increase indicates that the guiding cannula 260 has covered the hole 256 in the insufflation needle 250. The insufflation needle 250 may then be withdrawn completely from the guiding cannula 260. The valve 262 at the proximal end of the guiding cannula 260 prevents escape of gas from the peritoneal cavity.

Now that the guiding cannula 260 extends from the exterior of the patient into the peritoneal cavity, it may be used to guide the screw dilator 270 and adjustable length cannula 100 into the cavity. Using the guiding cannula 260 as a guidewire, the screw dilator 270 is inserted into the peritoneal cavity by applying pressure in a distal direction while rotating the screw dilator 270 and the cannula 100. Rotation causes the threads 282 of the screw dilator 270 as well as the threads 142 of the cannula 100 to screw through the fascia until the cannula 100 is properly seated. Rotation of both the screw dilator 270 and the cannula 100 results from interaction between the dilator fins 278 and the cannula notches 178. The screw dilator 270/cannula 100 will follow the path of the guiding cannula 260. Once the cannula 100 is in place, the guiding cannula 260 and the screw dilator 270 are removed from the central lumen of the cannula 100, which is now ready for the laparoscopic procedure.

It will be appreciated by those skilled in the art that the third insertion method of the present invention allows laparoscopic surgery to be performed through a single incision which is progressively widened by sequential insertion of the insufflation needle 250, the guiding cannula 260, the screw dilator 270, and the cannula 100. Furthermore, the guiding cannula 260 may be made from a soft, pliable plastic material so that no damage will be done to the bowel if the guiding cannula 260 is scraped across it. Once the guiding cannula 260 is in place and the insufflation needle 250 has been removed a fiber optic endoscope may be inserted into the peritoneal cavity through the guiding catheter 260 in order to visually verify that the abdominal organs are clear of the area in which the screw dilator 270 and cannula 100 will be placed. Therefore, the third insertion method of the present invention offers the significant advantage that the screw dilator 270 and cannula 100 are not inserted into the peritoneal cavity blindly. This will greatly reduce accidental injury to the abdominal organs during placement of the cannula 100.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. Specifically, the present invention has been illustrated in use with an abdominal wall, however those skilled in the art will appreciate that the present invention may be used to access any body cavity.

What is claimed is:

1. A method for inserting a cannula through a body cavity wall and into a body cavity, comprising the steps of:
   (a) providing an insufflation needle;
   (b) providing a guiding cannula;
   (c) providing a hollow dilator;
   (d) providing a second cannula;
   (e) inserting the insufflation needle through the body cavity wall such that a distal end of the insufflation needle extends into the body cavity;
   flowing gas through the insufflation needle and into the body cavity in order to insufflate the body cavity;
   (g) inserting the guiding cannula over the insufflation needle and through the body cavity wall such that a distal end of the guiding cannula extends into the body cavity wherein inserting the guiding cannula causes the guiding cannula to block the flow of gas through the insufflation needle; and
   (h) inserting the hollow dilator sleeved within the second cannula through the body cavity wall over the guiding cannula, such that a distal end of the dilator and a distal end of the second cannula extend into the body cavity.

2. The method of claim 1, further comprising the steps of:
   (i) withdrawing the guiding cannula from the body cavity; and
   (j) withdrawing the dilator from the body cavity.

3. The method of claim 1, further comprising the step of:
   (i) withdrawing the insufflation needle from the body cavity after performing step (g).

4. The method of claim 1, wherein step (c) further comprises providing a hollow dilator having a thread on a distal end thereof and wherein step (h) is performed by rotating the dilator such that a thread on the distal end of the dilator interacts with the body cavity wall in order to advance the dilator.

5. The method of claim 1, further comprising the step of:
   (i) inserting an endoscope through the guiding cannula and into the body cavity prior to performing step (h).

6. The method of claim 5, further comprising the step of:
   (j) viewing the body cavity through the endoscope prior to performing step (h) in order to ensure that insertion of the dilator and the second cannula will not harm any structures within the body cavity.

7. A method for inserting a cannula through a body cavity wall and into a body cavity, comprising the steps of:
 (a) providing an insufflation needle;
 (b) providing a guiding cannula;
 (c) providing a hollow dilator;
 (d) providing a second cannula;
 (e) inserting the insufflation needle through the body cavity wall such that an opening near a distal end of the insufflation needle is within the body cavity;
 (f) flowing gas through the opening and into the body cavity in order to insufflate the body cavity;
 (g) inserting the guiding cannula over the insufflation needle and through the body cavity wall such that a distal end of the guiding cannula is within the body cavity wherein inserting the guiding cannula substantially blocks further flow of gas through the insufflation needle;
 (h) withdrawing the insufflation needle from the body cavity;
 (i) inserting the dilator sleeved within the second cannula through the body cavity wall over the guiding cannula, such that a distal end of the dilator and a distal end of the second cannula extend into the body cavity;
 (j) withdrawing the guiding cannula from the body cavity; and
 (k) withdrawing the dilator from the body cavity.

8. The method of claim 7, wherein step (c) further comprises providing a hollow dilator having a thread on a distal end thereof and wherein step (i) is performed by rotating the dilator such that a thread on the distal end of the dilator interacts with the body cavity wall in order to advance the dilator.

9. The method of claim 7, further comprising the step of:
 (l) inserting an endoscope through the guiding cannula and into the body cavity prior to performing step (i).

10. The method of claim 9, further comprising the step of:
 (m) viewing the body cavity through the endoscope prior to performing step (i) in order to ensure that insertion of the dilator and the second cannula will not harm any structures within the body cavity.

11. A method for inserting a cannula through a body cavity wall and into a body cavity, comprising the step of:
 (a) sleeving a guiding cannula over an insufflation needle;
 (b) sleeving a dilator over the guiding cannula;
 (c) sleeving a second cannula over the dilator;
 (d) inserting the insufflation needle through the body cavity wall such that an opening near a distal end of the insufflation needle is within the body cavity;
 (e) flowing gas through the opening and into the body cavity in order to insufflate the body cavity;
 (f) advancing the guiding cannula over the insufflation needle and through the body cavity wall, wherein advancing the guiding cannula substantially blocks further flow of gas through the insufflation needle;
 (g) withdrawing the insufflation needle from the body cavity; and
 (h) advancing the dilator and the second cannula over the guiding cannula and through the body cavity wall.

12. The method of claim 11, further comprising the steps of:
 (i) withdrawing the guiding cannula from the body cavity; and
 (j) withdrawing the dilator from the body cavity.

13. The method of claim 11, wherein step (f) is performed until there is a substantial increase in a pressure of the gas.

14. The method of claim 11 wherein step (c) further comprises providing a hollow dilator having a thread on a distal end thereof and wherein step (h) is performed by rotating the dilator such that a thread on a distal end of the dilator interacts with the body cavity wall in order to advance the dilator.

15. The method of claim 11, further comprising the step of:
 (i) inserting an endoscope through the guiding cannula and into the body cavity prior to performing step (h).

16. The method of claim 15, further comprising the step of:
 (j) viewing the body cavity through the endoscope prior to performing step (h) in order to ensure that insertion of the dilator and the second cannula will not harm any structures within the body cavity.

17. A method for inserting a cannula through a body cavity wall and into a body cavity, comprising the steps of:
 (a) providing an insufflation needle;
 (b) providing a guiding cannula;
 (c) inserting the insufflation needle through the body cavity wall such that a distal end of the insufflation needle extends into the body cavity;
 (d) flowing gas through the insufflation needle and into the body cavity in order to insufflate the body cavity; and
 (e) inserting the guiding cannula over the insufflation needle and through the body cavity wall such that a distal end of the guiding cannula extends into the body cavity, wherein inserting the guiding cannula causes the guiding cannula to block the flow of gas through the insufflation needle.

18. The method of claim 17, wherein step (e) is performed until there is a substantial increase in a pressure of the gas.

19. The method of claim 17, further comprising the steps of:
 (f) providing a hollow dilator;
 (g) providing a second cannula; and
 (h) inserting the hollow dilator sleeved within the second cannula through the body cavity wall over the guiding cannula, such that a distal end of the dilator and a distal end of the second cannula extend into the body cavity.

20. The method of claim 19, further comprising the steps of:
 (i) withdrawing the guiding cannula from the body cavity; and
 (j) withdrawing the dilator from the body cavity.

21. The method of claim 19, wherein step (f) further comprises providing a hollow dilator having a thread on a distal end thereof and wherein step (h) is performed by rotating the dilator such that a thread on a distal end of the dilator interacts with the body cavity wall in order to advance the dilator.

22. The method of claim 19, further comprising the step of:
 (i) inserting an endoscope through the guiding cannula and into the body cavity prior to performing step (h).

23. The method of claim 22, further comprising the step of:
 (j) viewing the body cavity through the endoscope prior to performing step (h) in order to ensure that insertion of the dilator and the second cannula will not harm any structures within the body cavity.

* * * * *

UNITED STATES PATENT AND TRADEMARK OFFICE
CERTIFICATE OF CORRECTION

PATENT NO : 5,746,720

DATED : May 5, 1998

INVENTOR(S) : Albert E. Stouder, Jr.

It is certified that error appears in the above-identified patent and that said Letters Patent is hereby corrected as shown below:

In column 10, line 34, please insert --(f)-- and a tab prior to the word "flowing".
In column 11, line 16, please insert --,-- after the word "cavity".

Signed and Sealed this

Twenty-first Day of March, 2000

Attest:

Attesting Officer

Q. TODD DICKINSON

Commissioner of Patents and Trademarks